US008481513B2

(12) United States Patent
Bandarage et al.

(10) Patent No.: US 8,481,513 B2
(45) Date of Patent: Jul. 9, 2013

(54) 3, 10, AND 12A SUBSTITUTED TETRACYCLINE COMPOUNDS

(75) Inventors: Upul Bandarage, Lexington, MA (US); Jackson Chen, Williamsville, NY (US); Mohamed Y. Ismail, Bedford, MA (US); Mark L. Nelson, Norfolk, MA (US); Kwasi Ohemeng, Norwood, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 12/727,114

(22) Filed: Mar. 18, 2010

(65) Prior Publication Data

US 2010/0190756 A1 Jul. 29, 2010

Related U.S. Application Data

(63) Continuation of application No. 11/069,197, filed on Feb. 28, 2005, now Pat. No. 7,825,105, which is a continuation of application No. 10/853,537, filed on May 24, 2004, now abandoned, which is a continuation of application No. 10/619,653, filed on Jul. 14, 2003, now abandoned.

(60) Provisional application No. 60/395,696, filed on Jul. 12, 2002.

(51) Int. Cl.
*A01N 37/18* (2006.01)
*A61K 31/65* (2006.01)
*C07C 43/00* (2006.01)

(52) U.S. Cl.
USPC .......................................... 514/152; 552/203

(58) Field of Classification Search
None
See application file for complete search history.

(56) References Cited

U.S. PATENT DOCUMENTS

| | | | |
|---|---|---|---|
| 2,812,349 A | 11/1957 | Gordon et al. |
| 2,976,318 A | 3/1961 | Blackwood et al. |
| 3,043,876 A | 7/1962 | Rennhard et al. |
| 3,047,617 A | 7/1962 | Blackwood et al. |
| 3,165,531 A | 1/1965 | Nelson et al. |
| 5,567,692 A | 10/1996 | Sum et al. |
| 6,500,812 B2 | 12/2002 | Nelson et al. |
| 6,617,318 B1 | 9/2003 | Nelson et al. |
| 6,624,168 B2 | 9/2003 | Nelson et al. |
| 6,642,270 B2 | 11/2003 | Nelson et al. |
| 6,683,068 B2 | 1/2004 | Nelson et al. |
| 6,818,634 B2 | 11/2004 | Nelson et al. |
| 6,818,635 B2 | 11/2004 | Nelson et al. |
| 6,833,365 B2 | 12/2004 | Levy et al. |
| 6,841,546 B2 | 1/2005 | Draper et al. |
| 6,846,939 B2 | 1/2005 | Nelson et al. |
| 6,849,615 B2 | 2/2005 | Nelson et al. |
| 7,001,918 B2 | 2/2006 | Huss et al. |
| 7,045,507 B2 | 5/2006 | Draper et al. |
| 7,056,902 B2 | 6/2006 | Nelson et al. |
| 7,067,681 B2 | 6/2006 | Nelson et al. |
| 7,094,806 B2 | 8/2006 | Nelson et al. |
| 7,326,696 B2 | 2/2008 | Nelson et al. |
| 2002/0128237 A1 | 9/2002 | Nelson et al. |
| 2002/0128238 A1 | 9/2002 | Nelson et al. |
| 2004/0063674 A1 | 4/2004 | Levy et al. |
| 2004/0092490 A1 | 5/2004 | Draper et al. |
| 2004/0138183 A1 | 7/2004 | Nelson et al. |
| 2004/0176334 A1 | 9/2004 | Nelson et al. |
| 2004/0214800 A1 | 10/2004 | Levy et al. |
| 2004/0214801 A1 | 10/2004 | Nelson et al. |
| 2004/0242548 A1 | 12/2004 | Draper et al. |
| 2004/0266740 A1 | 12/2004 | Huss et al. |
| 2005/0020545 A1 | 1/2005 | Draper et al. |
| 2005/0026875 A1 | 2/2005 | Nelson et al. |
| 2005/0026876 A1 | 2/2005 | Nelson et al. |
| 2005/0038002 A1 | 2/2005 | Nelson et al. |
| 2005/0070510 A1 | 3/2005 | Draper et al. |
| 2005/0119235 A1 | 6/2005 | Nelson et al. |
| 2005/0137174 A1 | 6/2005 | Ohemeng et al. |
| 2005/0143352 A1 | 6/2005 | Nelson et al. |
| 2005/0143353 A1 | 6/2005 | Nelson et al. |
| 2005/0187198 A1 | 8/2005 | Nelson et al. |
| 2005/0215532 A1 | 9/2005 | Levy et al. |
| 2005/0250744 A1 | 11/2005 | Levy et al. |
| 2005/0282787 A1 | 12/2005 | Myers et al. |
| 2006/0003971 A1 | 1/2006 | Nelson |
| 2006/0084634 A1 | 4/2006 | Huss et al. |
| 2006/0089336 A1 | 4/2006 | Nelson et al. |
| 2006/0148765 A1 | 7/2006 | Nelson et al. |

(Continued)

FOREIGN PATENT DOCUMENTS

GB 766512 A 1/1957
GB 927739 A 6/1963

(Continued)

OTHER PUBLICATIONS

Wolff, Manfred E. "Burger's Medicinal Chemistry, 5ed, Part I", John Wiley & Sons, 1995, pp. 975-977.).*
Banker, G.S. et al, "Modern Pharmaceutics, 3ed.", Marcel Dekker, New York, 1996, pp. 451 and 596.*
Nelson et al., Journal of Medicinal Chemistry, 1994, 37(9), 1355-61.*
Database CAPLUS [Online], Chemical Abstracts Service, Columbus, Ohio, US; Rogalski et al., "Tetracyclic compounds", XP-002472903, retrieved from STN Database accession No. 1976:405501.
Database CAPLUS [Online], Chemical Abstracts Service, Columbus, Ohio, US; Pfizer, "Organic Nitriles", XP-002472893, retrieved from STN Database accession No. 1957:71706.

(Continued)

*Primary Examiner* — Traviss C McIntosh, III
(74) *Attorney, Agent, or Firm* — McCarter & English, LLP

(57) ABSTRACT

The present invention pertains to novel 3, 10, and/or 12a-substituted tetracycline compounds. These tetracycline compounds can be used to treat numerous tetracycline compound-responsive states, such as bacterial infections and neoplasms, as well as other known applications for minocycline and tetracycline compounds in general, such as blocking tetracycline efflux and modulation of gene expression.

24 Claims, No Drawings

U.S. PATENT DOCUMENTS

| | | | |
|---|---|---|---|
| 2006/0166944 A1 | 7/2006 | Berniac et al. | |
| 2006/0166945 A1 | 7/2006 | Abato et al. | |
| 2006/0166946 A1 | 7/2006 | Nelson et al. | |
| 2006/0194773 A1* | 8/2006 | Levy et al. | 514/152 |

FOREIGN PATENT DOCUMENTS

| | | |
|---|---|---|
| GB | 1100885 A | 1/1968 |
| GB | 1298508 A | 12/1972 |
| GB | 1464678 A | 2/1977 |
| GB | 1467206 A | 3/1977 |
| JP | 51-054564 A | 5/1976 |
| JP | 69522 | 1/1994 |
| NL | 6602413 A | 9/1966 |
| WO | WO-0174761 A1 | 10/2001 |
| WO | WO-0204406 A2 | 1/2002 |
| WO | WO-0204407 A2 | 1/2002 |
| WO | WO-02/072031 A2 | 9/2002 |
| WO | WO-02085303 A2 | 10/2002 |
| WO | WO-03/005971 A2 | 1/2003 |
| WO | WO-2004/006850 A2 | 1/2004 |
| WO | WO-2004/038000 A2 | 5/2004 |
| WO | WO-2004/038001 A2 | 5/2004 |
| WO | WO-2004/064728 A2 | 8/2004 |

OTHER PUBLICATIONS

Bartzatt, Ronald et al., "Synthesis and analysis of ethylated tetracyclinem, an antibiotic derivative that inhibits the growth of tetracycline-resistant XL I-Blue bacteria," *Biotechnol. Appl. Biochem.*, vol. 33:65-69 (2001).

Bartzatt, Ronald et al., "Synthesis and Analysis of a Methyl Ether Derivative of Tetracycine Which Inhibits Growth of *Escherichia coli*," *Physiol. Chem. Phys. & Med. NMR*, vol. 34:71-81 (2002).

McCormick, J.R.D. et al., "On the Nature of the Reversible Isomerizations Occurring in the Tetracycline Family," *Journal of the American Chemical Society*, vol. 78(14):3547-3548 (1956).

Nelson, Mark L. et al., "Molecular Requirements for the Inhibition of the Tetracycline Antiport Protein and the Effect of Potent Inhibitors on the Growth of Tetracycline-Resistant Bacteria," *J. Med. Chem.*, vol. 37:1355-1361 (1994).

Stephens, Charles R. et al., "6-Deoxytetracyclines. IV. Preparation, C-6 Stereochemistry, and Reactions," *Journal of the American Chemical Society*, vol. 85(17):2643-2652 (1963).

CAPLUS AN 1994:217052, Sum, P.-E. et al, "Glycylcyclines. 1. A new generation of potent antibacterial agents through modification of 9-aminotetracyclines," *Journal of Medicinal Chemistry*, vol. 37(1):184-188 (1994).

Sum, Phaik-Eng et al, "Glycylcyclines. 1. A New Generation of Potent Antibacterial Agents through Modification of 9-Aminotetracyclines," *J. Med. Chem.*, vol. 37:184-188 (1994).

Bu'Lock, J. D, et al. "Bikaverin and norbikaverin, benzoxanthenetrione pigments of *Gibberella fujikuroi*", *Journal of the Chemical Society* [Section] C: Organic, 1971, (16), 2792-7.

De Koning, C. B, et al. "Convenient syntheses of the naturally occuring benzo[b]xanthen-12-one bikaverin. X-ray crystallographic confirmation of the product regiochemistry", *Journal of the Chemical Society, Perkin Transactions 1: Organic and Bio-Organic Chemistry*, 1988, (12), 3209-16.

Deshpande, V. H., et al. "Regiospecific synthesis of bikaverin", *Synthetic Communications*, 1993, 23(19), 2677-82.

\* cited by examiner

3, 10, AND 12A SUBSTITUTED TETRACYCLINE COMPOUNDS

RELATED APPLICATION

This application is a continuation of U.S. Ser. No. 11/069,197, now U.S. Pat. No. 7,825,105, filed Feb. 28, 2005, which is a continuation of U.S. Ser. No. 10/853,537, abandoned, filed May 24, 2004, which is a continuation of U.S. Ser. No. 10/619,653, abandoned, filed Jul. 14, 2003, which claims priority to U.S. Pro. Appl. No. 60/395,696, filed Jul. 12, 2002, the entire contents of each of which are incorporated herein by reference.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 2,980,584; 2,990,331; 3,062,717; 3,165,531; 3,454,697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., pneumococci and *Salmonella*). The rise of tetracycline-resistant organisms has resulted in a general decline in use of tetracyclines and tetracycline analogue compositions as antibiotics of choice.

SUMMARY OF THE INVENTION

In one embodiment, the invention pertains, at least in part, to tetracycline compounds of Formula I:

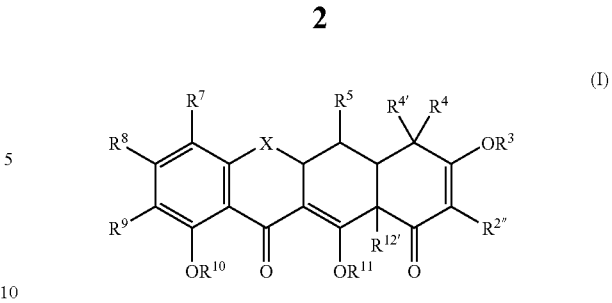

wherein:
X is CHC($R^{13}$Y'Y), CR$^{6'}$R$^6$, S, NR$^6$, or O;
R$^{2''}$ is —C(=O)NR$^2$R$^{2'}$, or —CN;
R$^2$, R$^{2'}$, R$^{4a}$, and R$^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
R$^3$, R$^{10}$, R$^{11}$, R$^{12}$, and R$^{12''}$ are each independently hydrogen, alkyl, alkenyl, aryl, alkynyl, aralkyl, acetyl, alkylcarbonyl, alkenylcarbonyl, arylcarbonyl, alkynylcarbonyl, alkyloxycarbonyl, alkenyloxycarbonyl, alkynyloxycarbonyl, aryloxycarbonyl, alkylaminocarbonyl, alkenylaminocarbonyl, alkynylaminocarbonyl, arylaminocarbonyl, alkylthiocarbonyl, alkenylthiocarbonyl, alkynylthiocarbonyl, arylthiocarbonyl, alkyloxythiocarbonyl, alkenyloxythiocarbonyl, alkynyloxythiocarbonyl, aryloxythiocarbonyl, alkylaminothiocarbonyl, alkenylaminothiocarbonyl, alkynylaminothiocarbonyl, arylaminothiocarbonyl, alkylthiothiocarbonyl, alkenylthiothiocarbonyl, alkynylthiothiocarbonyl, arylthiothiocarbonyl, provided that at least one of R$^3$, R$^{10}$, R$^{11}$, or R$^{12}$ is not hydrogen when R$^2$ is —C(=O)NR$^2$R$^{2'}$;
R$^4$ and R$^{4'}$ are each independently NR$^{4a}$R$^{4b}$, alkyl, alkenyl, alkynyl, hydroxyl, halogen, hydrogen, or when taken together the oxygen of a carbonyl group;
R$^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
R$^6$ and R$^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
R$^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —(CH$_2$)$_{0-3}$NR$^{7c}$C(=W')WR$^{7a}$;
R$^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or —(CH$_2$)$_{0-3}$NR$^{8c}$C(=E')ER$^{8a}$;
R$^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, —(CH$_2$)$_{0-3}$NR$^{9c}$C(=Z')ZR$^{9a}$, or R$^9$ is optionally linked to R$^{10}$ to form a heterocyclic ring;
R$^{7a}$, R$^{7b}$, R$^{7c}$, R$^{7d}$, R$^{7e}$, R$^{7f}$, R$^{8a}$, R$^{8b}$, R$^{8c}$, R$^{8d}$, R$^{8e}$, R$^{8f}$, R$^{9a}$, R$^{9b}$, R$^{9c}$, R$^{9d}$, R$^{9e}$, and R$^{8f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
R$^{12'}$ is OR$^{12}$ or NR$^{12}$R$^{12''}$;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl;

E is $CR^{8d}R^{8e}$, S, $NR^{8b}$ or O;

E' is O, $NR^{8f}$, or S;

W is $CR^{7d}R^{7e}$, S, $NR^{7b}$ or O;

W' is O, $NR^{7f}$, or S;

X is $CHC(R^{13}Y'Y)$, $C=CR^{13}Y$, $CR^{6'}R^6$, S, $NR^6$, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is $CR^{9d}R^{9e}$, S, $NR^{9b}$ or O;

Z' is O, S, or $NR^{9f}$, and pharmaceutically acceptable salts, esters and enantiomers thereof.

The invention also pertains, at least in part, to methods for derivatizing tetracycline compounds at the 3-position, 10, position, and/or 12a position. The methods include contacting a tetracycline compound with an appropriate base under appropriate first conditions, and contacting the tetracycline compound with a derivatizing reagent under appropriate second conditions.

The invention also pertains, at least in part, to methods for dederivatizing a derivatized tetracycline compound (e.g., a tetracycline compound derivatized at the 3-position, 10-position, and/or 12a-position). The method includes contacting the derivatized tetracycline compound with an appropriate dederivatizing agent under appropriate conditions, such that derivatized tetracycline compound is dederivatized.

In another embodiment, the invention pertains, at least in part, to methods for treating a tetracycline responsive state in a subject, by administering to the subject a tetracycline compound of the invention.

In a further embodiment, the invention also pertains to pharmaceutical compositions, which contain a therapeutically effective amount of a tetracycline compound of the invention or mixtures thereof, and a pharmaceutically acceptable carrier.

DETAILED DESCRIPTION OF THE INVENTION

The invention pertains, at least in part, to tetracycline compounds of Formula I:

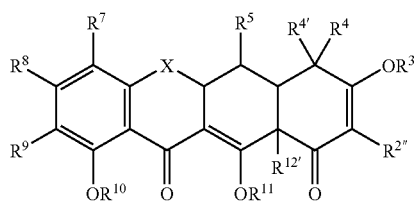

(I)

wherein:

X is $CHC(R^{13}Y'Y)$, $CR^{6'}R^6$, S, $NR^6$, or O;

R2''' is $-C(=O)NR^2R^{2'}$, or $-CN$;

$R^2$, $R^{2'}$, $R^{4a}$, and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^3$, $R^{10}$, $R^{11}$, $R^{12}$, and $R^{12''}$ are each independently hydrogen, alkyl, alkenyl, aryl, alkynyl, aralkyl, acetyl, alkylcarbonyl, alkenylcarbonyl, arylcarbonyl, alkynylcarbonyl, alkyloxycarbonyl, alkenyloxycarbonyl, alkynyloxycarbonyl, aryloxycarbonyl, alkylaminocarbonyl, alkenylaminocarbonyl, alkynylaminocarbonyl, arylaminocarbonyl, alkylthiocarbonyl, alkenylthiocarbonyl, alkynylthiocarbonyl, arylthiocarbonyl, alkyloxythiocarbonyl, alkenyloxythiocarbonyl, alkynyloxythiocarbonyl, aryloxythiocarbonyl, alkylaminothiocarbonyl, alkenylaminothiocarbonyl, alkynylaminothiocarbonyl, arylaminothiocarbonyl, alkylthiothiocarbonyl, alkenylthiothiocarbonyl, alkynylthiothiocarbonyl, arylthiothiocarbonyl, provided that at least one of $R^3$, $R^{10}$, $R^{11}$, or $R^{12}$ is not hydrogen when $R^2$ is $-C(=O)NR^2R^{2'}$;

$R^4$ and $R^{4'}$ are each independently $NR^{4a}R^{4b}$, alkyl, alkenyl, alkynyl, hydroxyl, halogen, hydrogen, or when taken together the oxygen of a carbonyl group;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}NR^{7c}C(=W')WR^{7a}$;

$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or $-(CH_2)_{0-3}NR^{8c}C(=E')ER^{8a}$;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}NR^{9c}C(=Z')ZR^{9a}$;

$R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$, and $R^{8f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{12'}$ is $OR^{12}$ or $NR^{12}R^{12''}$;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl;

E is $CR^{8d}R^{8e}$, S, $NR^{8b}$ or O;

E' is O, $NR^{8f}$, or S;

W is $CR^{7d}R^{7e}$, S, $NR^{7b}$ or O;

W' is O, $NR^{7f}$, or S;

X is $CHC(R^{13}Y'Y)$, $C=CR^{13}Y$, $CR^{6'}R^6$, S, $NR^6$, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is $CR^{9d}R^{9e}$, S, $NR^{9b}$ or O;

Z' is O, S, or $NR^{9f}$, and pharmaceutically acceptable salts, esters and enantiomers thereof.

The term "tetracycline compound" includes many compounds with a similar ring structure to tetracycline. Examples of tetracycline compounds include: tetracycline, oxytetracycline, chlortetracycline, demeclocycline, doxycycline, chelocardin, minocycline, rolitetracycline, lymecycline, sancycline, methacycline, apicycline, clomocycline, guamecycline, meglucycline, mepylcycline, penimepicycline, pipacycline, etamocycline, and penimocycline. Other derivatives and analogues comprising a similar four ring structure are also included. The term includes 4-dedimethylamino derivatives. Table 1 depicts tetracycline and several known tetracycline derivatives. The tetracycline compounds may be unsubstituted at any position or further substituted, for example, at the 2, 4, 5, 6, 7, 8, 9, or 13 position of the ring.

TABLE I

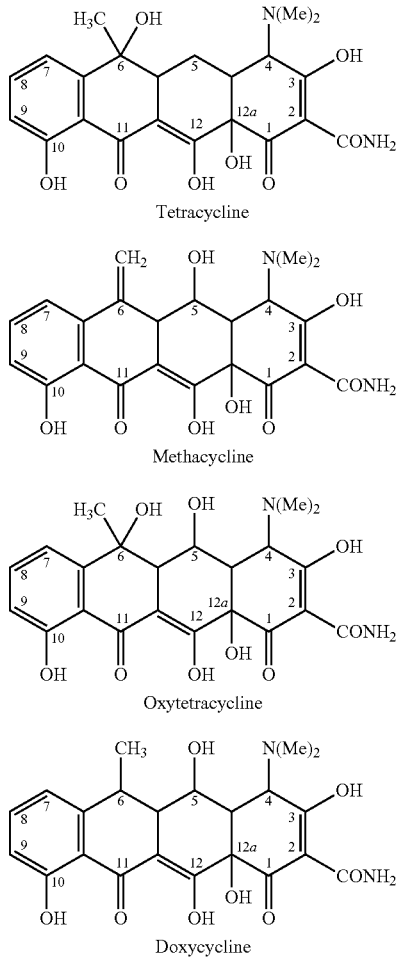

Tetracycline

Methacycline

Oxytetracycline

Doxycycline

The term "substituted tetracycline compounds" includes tetracycline compounds with substitution at the 3, 10, and/or 12a-position of the tetracycline molecule other than hydroxy. In one embodiment, the substitution enhances the ability of the tetracycline compound to perform its intended function, e.g., treat tetracycline responsive states. In an embodiment, the substituted tetracycline compound is substituted tetracycline (e.g., wherein $R^4$ is $NR^{4a}R^{4b}$; $R^{4a}$ and $R^{4b}$ are methyl, $R^5$ is hydrogen and X is $CR^6R^{6'}$, wherein $R^6$ is methyl and $R^{6'}$ is hydroxy); substituted doxycycline (e.g., wherein $R^4$ is $NR^{4a}R^{4b}$; $R^{4a}$ and $R^{4b}$ are methyl, $R^5$ is hydroxyl and X is $CR^6R^{6'}$, wherein $R^6$ is methyl and $R^{6'}$ is hydrogen); or substituted sancycline (wherein $R^4$ is $NR^{4a}R^{4b}$; $R^{4a}$ and $R^{4b}$ are methyl; $R^5$ is hydrogen and X is $CR^6R^{6'}$ wherein $R^6$ and $R^{6'}$ are hydrogen atoms. In one embodiment, $R^4$ and $R^{4'}$ are each hydrogen or the oxygen of a carbonyl group. In an embodiment, the compounds of the invention do not include compounds wherein $R^{10}$ is a sugar or compounds described in DD 268 951, incorporated herein by reference in its entirety.

The tetracycline compounds of the invention include, for example, compounds wherein X is $CR^6R^{6'}$; $R^4$ and $R^{4'}$ are hydrogen or the oxygen of a carbonyl group; $R^2$, $R^{2'}$, $R^6$, $R^{6'}$, $R^8$, $R^{10}$, $R^{11}$, and $R^{12}$ are each hydrogen; and $R^{4a}$ and $R^{4b}$ are lower alkyl; and $R^5$ is hydroxy or hydrogen. In an embodiment, $R^4$ and $R^{4'}$ are each hydrogen and $R^5$ is hydrogen. In a further embodiment, the compounds of the invention include compounds wherein $R^4$ is dialkylamino, $R^{4'}$ is hydrogen and $R^5$ is hydrogen.

In one embodiment, the tetracycline compounds of the invention include tetracycline compounds of formula (I), wherein $R^3$ is alkyl, alkenyl, aryl, acetyl, aralkyl, alkynyl, alkylcarbonyl, alkenylcarbonyl, arylcarbonyl, alkynylcarbonyl, alkyloxycarbonyl, alkenyloxycarbonyl, alkynyloxycarbonyl, aryloxycarbonyl, alkylaminocarbonyl, alkenylaminocarbonyl, alkynylaminocarbonyl, arylaminocarbonyl, alkylthiocarbonyl, alkenylthiocarbonyl, alkynylthiocarbonyl, arylthiocarbonyl, alkyloxythiocarbonyl, alkenyloxythiocarbonyl, alkynyloxythiocarbonyl, aryloxythiocarbonyl, alkylaminothiocarbonyl, alkenylaminothiocarbonyl, alkynylaminothiocarbonyl, arylaminothiocarbonyl, alkylthiothiocarbonyl, alkenylthiothiocarbonyl, alkynylthiothiocarbonyl, or arylthiothiocarbonyl.

In a further embodiment, $R^3$ is aralkyl, e.g., benzyl. In another further embodiment, $R^3$ is alkyl, alkenyl, or acetyl. In another further embodiment (e.g., when $R^{10}$ and $R^{12a}$ are not both hydrogen), $R^3$ is hydrogen.

In one embodiment, the tetracycline compounds of the invention include tetracycline compounds of formula (I), wherein $R^{10}$ is alkyl, alkenyl, aryl, acetyl, aralkyl, alkynyl, alkylcarbonyl, alkenylcarbonyl, arylcarbonyl, alkynylcarbonyl, alkyloxycarbonyl, alkenyloxycarbonyl, alkynyloxycarbonyl, aryloxycarbonyl, alkylaminocarbonyl, alkenylaminocarbonyl, alkynylaminocarbonyl, arylaminocarbonyl, alkylthiocarbonyl, alkenylthiocarbonyl, alkynylthiocarbonyl, arylthiocarbonyl, alkyloxythiocarbonyl, alkenyloxythiocarbonyl, alkynyloxythiocarbonyl, aryloxythiocarbonyl, alkylaminothiocarbonyl, alkenylaminothiocarbonyl, alkynylaminothiocarbonyl, arylaminothiocarbonyl, alkylthiothiocarbonyl, alkenylthiothiocarbonyl, alkynylthiothiocarbonyl, or arylthiothiocarbonyl.

In a further embodiment, $R^{10}$ is aralkyl, e.g., benzyl. In another further embodiment, $R^{10}$ is alkyl, alkenyl, or acetyl. In another further embodiment (e.g., when $R^3$ and $R^{12}$ are not both hydrogen), $R^{10}$ is hydrogen.

In one embodiment, the tetracycline compounds of the invention include tetracycline compounds of formula (I), wherein $R^{12}$ is alkyl, alkenyl, aryl, acetyl, aralkyl, alkynyl, alkylcarbonyl, alkenylcarbonyl, arylcarbonyl, alkynylcarbonyl, alkyloxycarbonyl, alkenyloxycarbonyl, alkynyloxycarbonyl, aryloxycarbonyl, alkylaminocarbonyl, alkenylaminocarbonyl, alkynylaminocarbonyl, arylaminocarbonyl, alkylthiocarbonyl, alkenylthiocarbonyl, alkynylthiocarbonyl, arylthiocarbonyl, alkyloxythiocarbonyl, alkenyloxythiocarbonyl, alkynyloxythiocarbonyl, aryloxythiocarbonyl, alkylaminothiocarbonyl, alkenylaminothiocarbonyl, alkynylaminothiocarbonyl, arylaminothiocarbonyl, alkylthiothiocarbonyl, alkenylthiothiocarbonyl, alkynylthiothiocarbonyl, or arylthiothiocarbonyl.

In a further embodiment, $R^{12}$ is aralkyl, e.g., benzyl. In another further embodiment, $R^{12}$ is alkyl, alkenyl, or acetyl. In another further embodiment (e.g., when $R^3$ and $R^{10}$ are not both hydrogen), $R^{12}$ is hydrogen.

In one embodiment, $R^{2''}$ is cyano.

In another embodiment, $R^{12'}$ is $NR^{12'}R^{12''}$. $R^{12'}$ may be alkyl and $R^{12''}$ may be hydrogen.

Examples of compounds of the invention include, but are not limited to:

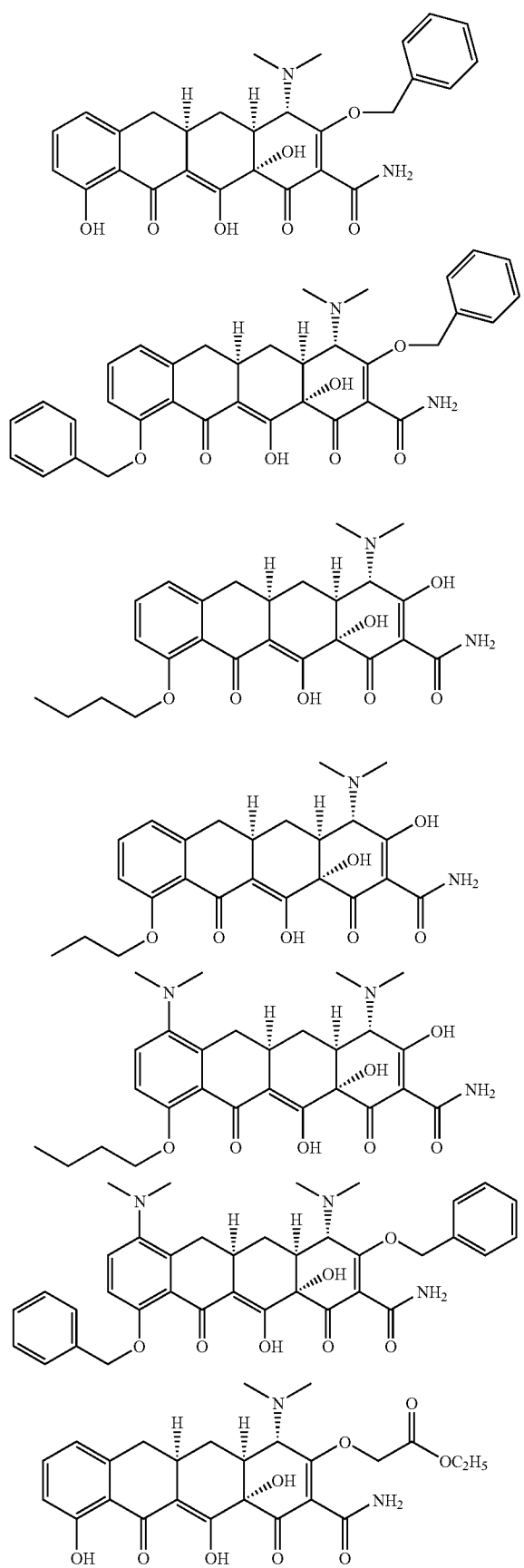
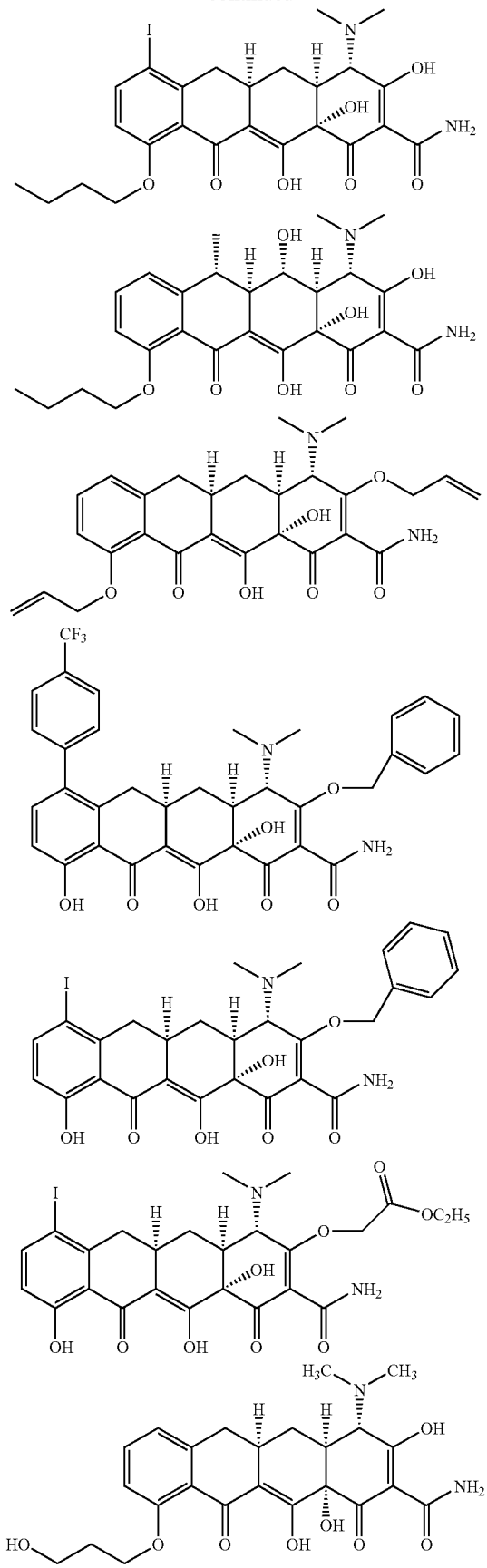

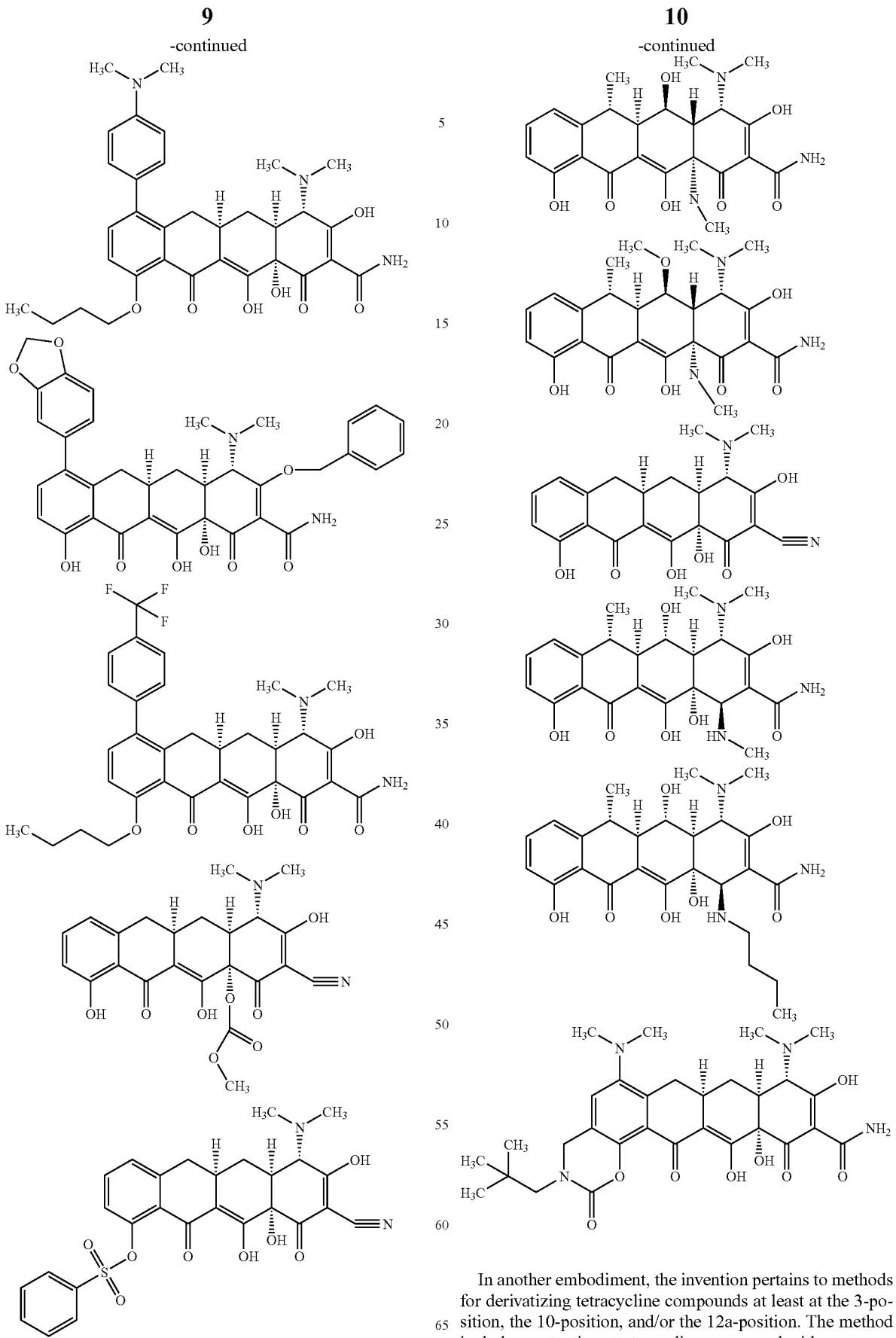
In another embodiment, the invention pertains to methods for derivatizing tetracycline compounds at least at the 3-position, the 10-position, and/or the 12a-position. The method includes contacting a tetracycline compound with an appropriate base under appropriate first conditions, and contacting the tetracycline compound with a derivatizing reagent under appropriate second conditions, such that said tetracycline compound is derivatized. The 3-position, 10-position and 12a-position are shown on the tetracycline structure below.

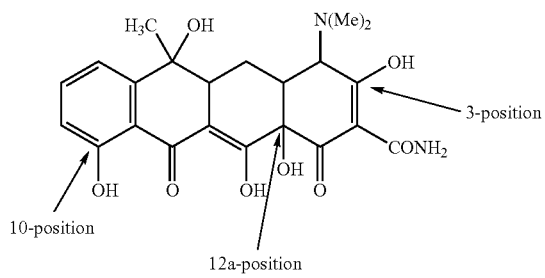

The term "derivatizing" includes changing the substituents at the 3-, 10-, and/or 12a position to a substituent other than hydroxyl. The tetracycline compound may be derivatized by contacting it with an appropriate base under appropriate conditions.

Examples of appropriate bases include bases which are capable of deprotonating the 3-, 10-, and/or 12a hydroxyl groups. Examples of such bases include sodium hydride. Preferably, the base is selectively deprotonates the tetracycline compound at a particular position, such that the resulting derivatized tetracycline compound is relatively free of positional isomers. Other bases which may be used include potassium hydride and sodium hydroxide.

The term "appropriate first conditions" include conditions in which the base can interact with the tetracycline compound, and deprotonate the desired hydroxyl group. In one embodiment, the appropriate first conditions comprise an aprotic solvent. Examples of suitable solvents include dimethylformamide (DMF), and other aprotic solvents. The appropriate first conditions may also comprise altering the temperature of the reaction components. In certain embodiments, the tetracycline compound and the appropriate base are allowed to react at room temperature for an appropriate length of time. One of ordinary skill in the art will be able to use art recognized techniques to determine the length of time needed to allow the reaction to near completion. Preferably, the appropriate first conditions are selected such that the solvent and the atmosphere are inert to the tetracycline compound and base.

The term "derivatizing agent" includes agents which can react with the tetracycline compound (after being treated with an appropriate base), to form a derivatized tetracycline compound (e.g., a tetracycline compound with a substituent at the 3, 10, or 12a position). Examples of derivatizing agents include, but are not limited to, alkyl halides, alkenyl halides, alkynyl halides, acid halides, isocyanates, isothiocyanates, esters, carbonates, silyl halides (e.g., silyl chlorides), ketones, aldehydes, Mannich bases, diazonium compounds, and their salts.

The term "appropriate second conditions" include conditions which allow derivatizing agents to interact with tetracycline compounds (optionally deprotonated) to form derivatized tetracycline compounds. Preferably, the appropriate first conditions are selected such that the conditions (including, for example, the solvent and the atmosphere) are inert to the derivatizing agent, the tetracycline compound, and the base. In certain embodiments, the appropriate second conditions may be the same, different, or partially the same and partially different than the appropriate first conditions. For example, in certain embodiments, the appropriate second conditions may comprise heating the reaction mixture. An ordinarily skilled artisan will be able to determine using art recognized techniques the appropriate length of time and temperature for the reaction to take place.

In a further embodiment, the invention pertains to a method for dederivatizing a derivatized tetracycline compound (e.g., a tetracycline compound derivatized at the 3-position, 10-position, and/or 12a-position). The method includes contacting a derivatized tetracycline compound with an appropriate dederivatizing agent under appropriate conditions, such that derivatized tetracycline compound is dederivatized.

Examples of dederivatizing agents include agents which can alter the derivatized tetracycline compounds to tetracycline compound without the derivatization at one or more positions of the tetracycline molecule. Examples of such agents include, for example, acids, or other hydrolysis or deprotection methods known in the art. In certain embodiments, substituents at position 3, 10, and/or 12a are hydroxyl or O— after being treated with a dederivatizing agent under appropriate conditions.

The term "appropriate conditions" include reaction conditions (e.g., atmosphere, solvent, temperature, time, etc.) which allow the reaction to take place. An ordinarily skilled artisan will be able to manipulate the reaction conditions to obtain a desired result.

In certain embodiments, the tetracycline compounds may be dederivatized after altering one or more substituents on the tetracycline compound. The substituents which may be altered include any substituent which can be altered on the tetracycline compound. Examples of such reactions which can be done on the derivatized or underivatized tetracycline compound include those described in, for example, U.S. Ser. No. 09/895,857; U.S. Ser. No. 09/895,812; U.S. Pat. No. 5,326,759; U.S. Pat. No. 5,328,902; U.S. Pat. No. 5,495,031; U.S. Pat. No. 5,495,018; U.S. Pat. No. 5,495,030; U.S. Pat. No. 5,495,032; U.S. Pat. No. 5,512,553; U.S. Pat. No. 5,675,030; U.S. Pat. No. 5,843,925; U.S. Pat. No. 5,886,175; U.S. Pat. No. 6,165,999; U.S. Pat. No. 3,239,499; WO 95/22529; U.S. Pat. No. 5,064,821; U.S. Pat. No. 5,589,470; and U.S. Pat. No. 5,811,412, all incorporated herein by reference. In an embodiment, the present invention also pertains to 3, 10, and/or 12a derivatives of each of the tetracycline compounds disclosed in each of the above references.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxophenyl, quinoline, isoquinoline, naphthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO-$) or a carbonyl group. It includes substituted acyl moieties. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "carbonyl" or "carboxy" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters.

It will be noted that the structure of some of the tetracycline compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

The invention also pertains to methods for treating a tetracycline responsive states in subjects, by administering to a subject an effective amount of a tetracycline compound of the invention (e.g., a compound of Formula (I)), such that the tetracycline responsive state is treated.

The term "treating" includes curing as well as ameliorating at least one symptom of the state, disease or disorder, e.g., the tetracycline compound responsive state.

The language "tetracycline compound responsive state" or "tetracycline responsive state" includes states which can be treated, prevented, or otherwise ameliorated by the administration of a tetracycline compound of the invention, e.g., a 3, 10, and/or 12a substituted tetracycline compound. Tetracycline compound responsive states include bacterial, viral, and fungal infections (including those which are resistant to other tetracycline compounds), cancer (e.g., prostate, breast, colon, lung melanoma and lymph cancers and other disorders characterized by unwanted cellular proliferation, including, but not limited to, those described in U.S. Pat. No. 6,100,248), arthritis, osteoporosis, diabetes, and other states for which tetracycline compounds have been found to be active (see, for example, U.S. Pat. Nos. 5,789,395; 5,834,450; 6,277,061 and 5,532,227, each of which is expressly incorporated herein by reference). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., *Cancer Res.*, 48:6686-6690 (1988)). In a further embodiment, the tetracycline responsive state is not a bacterial infection. In another embodiment, the tetracycline compounds of the invention are essentially non-antibacterial. For example, non-antibacterial tetracycline compounds of the invention may have MIC values greater than about 4 μg/ml (as measured by assays known in the art and/or the assay given in Example 2).

Tetracycline compound responsive states also include inflammatory process associated states (IPAS). The term "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, lasting only a few days. If it is longer lasting however, then it may be referred to as chronic inflammation.

IPAF's include inflammatory disorders. Inflammatory disorders are generally characterized by heat, redness, swelling, pain and loss of function. Examples of causes of inflammatory disorders include, but are not limited to, microbial infections (e.g., bacterial and fungal infections), physical agents (e.g., burns, radiation, and trauma), chemical agents (e.g., toxins and caustic substances), tissue necrosis and various types of immunologic reactions.

Examples of inflammatory disorders include, but are not limited to, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

Tetracycline compound responsive states also include NO associated states. The term "NO associated state" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention, e.g., a 3, 10, and/or 12a substituted tetracycline compound. The disorders, diseases and states described in U.S. Pat. Nos. 6,231,894; 6,015,804; 5,919,774; and 5,789,395 are also included as NO associated states. The entire contents of each of these patents are hereby incorporated herein by reference.

Other examples of NO associated states include, but are not limited to, malaria, senescence, diabetes, vascular stroke, neurodegenerative disorders (Alzheimer's disease & Huntington's disease), cardiac disease (reperfusion-associated injury following infarction), juvenile diabetes, inflammatory disorders, osteoarthritis, rheumatoid arthritis, acute, recurrent and chronic infections (bacterial, viral and fungal); acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendonitis); uremic pericarditis; acute and chronic cholecystis; cystic fibrosis, acute and chronic vaginitis; acute and chronic uveitis; drug reactions; insect bites; burns (thermal, chemical, and electrical); and sunburn.

The term "inflammatory process associated state" also includes, in one embodiment, matrix metalloproteinase associated states (MMPAS). MMPAS include states characterized by aberrant amounts of MMPs or MMP activity. These are also include as tetracycline compound responsive states which may be treated using compounds of the invention, e.g., 3, 10, and/or 12a substituted tetracycline compounds.

Examples of matrix metalloproteinase associated states ("MMPAS's") include, but are not limited to, arteriosclerosis, corneal ulceration, emphysema, osteoarthritis, multiple sclerosis (Liedtke et al., *Ann. Neurol.* 1998, 44:35-46; Chandler et al., *J. Neuroimmunol.* 1997, 72:155-71), osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion (Stetler-Stevenson et al., *Annu. Rev. Cell Biol.* 1993, 9:541-73; Tryggvason et al., *Biochim. Biophys. Acta* 1987, 907:191-217; Li et al., *Mol. Carcinog.* 1998, 22:84-89)), metastasis, acute lung injury, stroke, ischemia, diabetes, aortic or vascular aneurysms, skin tissue wounds, dry eye, bone and cartilage degradation (Greenwald et al., *Bone* 1998, 22:33-38; Ryan et al., *Curr. Op. Rheumatol.* 1996, 8; 238-247). Other MMPAS include those described in U.S. Pat. Nos. 5,459,135; 5,321,017; 5,308,839; 5,258,371; 4,935,412; 4,704,383, 4,666,897, and RE 34,656, incorporated herein by reference in their entirety.

In another embodiment, the tetracycline compound responsive state is cancer. Examples of cancers which the tetracycline compounds of the invention may be useful to treat include all solid tumors, i.e., carcinomas e.g., adenocarcinomas, and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Examples of carcinomas which may be treated using the methods of the invention include, but are not limited to, carcinomas of the prostate, breast, ovary, testis, lung, colon, and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostatic carcinoma, lung cancer, and a variety of other cancers as well. The methods of the invention also cause the inhibition of cancer growth in adenocarcinomas, such as, for example, those of the prostate, breast, kidney, ovary, testes, and colon.

In an embodiment, the tetracycline responsive state of the invention is cancer. The invention pertains to a method for treating a subject suffering or at risk of suffering from cancer, by administering an effective amount of a substituted tetracycline compound, such that inhibition cancer cell growth occurs, i.e., cellular proliferation, invasiveness, metastasis, or tumor incidence is decreased, slowed, or stopped. The inhibition may result from inhibition of an inflammatory process, down-regulation of an inflammatory process, some other mechanism, or a combination of mechanisms. Alternatively, the tetracycline compounds may be useful for preventing cancer recurrence, for example, to treat residual cancer following surgical resection or radiation therapy. The tetracycline compounds useful according to the invention are especially advantageous as they are substantially non-toxic compared to other cancer treatments. In a further embodiment, the compounds of the invention are administered in combination with standard cancer therapy, such as, but not limited to, chemotherapy.

Examples of tetracycline responsive states also include neurological disorders which include both neuropsychiatric and neurodegenerative disorders, but are not limited to, such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amylotrophic lateral sclerosis (ALS), progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, Korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), bipolar affective neurological disorders, e.g., migraine and obesity. Further neurological disorders include, for example, those listed in the American Psychiatric Association's Diagnostic and Statistical manual of Mental Disorders (DSM), the most current version of which is incorporated herein by reference in its entirety.

The language "in combination with" another therapeutic agent or treatment includes co-administration of the tetracycline compound, (e.g., inhibitor) and with the other therapeutic agent or treatment, administration of the tetracycline compound first, followed by the other therapeutic agent or treatment and administration of the other therapeutic agent or treatment first, followed by the tetracycline compound. The other therapeutic agent may be any agent who is known in the art to treat, prevent, or reduce the symptoms of an IPAS. Furthermore, the other therapeutic agent may be any agent of benefit to the patient when administered in combination with the administration of an tetracycline compound. In one embodiment, the cancers treated by methods of the invention include those described in U.S. Pat. Nos. 6,100,248; 5,843, 925; 5,837,696; or 5,668,122, incorporated herein by reference in their entirety.

In another embodiment, the tetracycline compound responsive state is diabetes, e.g., juvenile diabetes, diabetes mellitus, diabetes type I, or diabetes type II. In a further embodiment, protein glycosylation is not affected by the administration of the tetracycline compounds of the invention. In another embodiment, the tetracycline compound of the invention is administered in combination with standard diabetic therapies, such as, but not limited to insulin therapy. In a further embodiment, the IPAS includes disorders described in U.S. Pat. Nos. 5,929,055; and 5,532,227, incorporated herein by reference in their entirety.

In another embodiment, the tetracycline compound responsive state is a bone mass disorder. Bone mass disorders include disorders where a subjects bones are disorders and states where the formation, repair or remodeling of bone is advantageous. For examples bone mass disorders include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the tetracycline compounds of the invention. In a further embodiment, the bone mass disorders include those described in U.S. Pat. Nos. 5,459,135; 5,231,017; 5,998,390; 5,770,588; RE 34,656; 5,308,839; 4,925,833; 3,304,227; and 4,666,897, each of which is hereby incorporated herein by reference in its entirety.

In another embodiment, the tetracycline compound responsive state is acute lung injury. Acute lung injuries include adult respiratory distress syndrome (ARDS), post-pump syndrome (PPS), and trauma. Trauma includes any injury to living tissue caused by an extrinsic agent or event. Examples of trauma include, but are not limited to, crush injuries, contact with a hard surface, or cutting or other damage to the lungs.

The invention also pertains to a method for treating acute lung injury by administering a substituted tetracycline compound of the invention.

The tetracycline responsive states of the invention also include chronic lung disorders. The invention pertains to methods for treating chronic lung disorders by administering a tetracycline compound, such as those described herein. The method includes administering to a subject an effective amount of a substituted tetracycline compound such that the chronic lung disorder is treated. Examples of chronic lung disorders include, but are not limited, to asthma, cystic fibrosis, and emphysema. In a further embodiment, the tetracycline compounds of the invention used to treat acute and/or chronic lung disorders such as those described in U.S. Pat. Nos. 5,977,091; 6,043,231; 5,523,297; and 5,773,430, each of which is hereby incorporated herein by reference in its entirety.

In yet another embodiment, the tetracycline compound responsive state is ischemia, stroke, or ischemic stroke. The invention also pertains to a method for treating ischemia, stroke, or ischemic stroke by administering an effective amount of a substituted tetracycline compound of the invention. In a further embodiment, the tetracycline compounds of the invention are used to treat such disorders as described in U.S. Pat. Nos. 6,231,894; 5,773,430; 5,919,775 or 5,789,395, incorporated herein by reference.

In another embodiment, the tetracycline compound responsive state is a skin wound. The invention also pertains, at least in part, to a method for improving the healing response of the epithelialized tissue (e.g., skin, mucusae) to acute traumatic injury (e.g., cut, burn, scrape, etc.). The method may include using a tetracycline compound of the invention (which may or may not have antibacterial activity) to improve the capacity of the epithelialized tissue to heal acute wounds. The method may increase the rate of collagen accumulation of the healing tissue. The method may also decrease the proteolytic activity in the epthithelialized tissue by decreasing the collagenolytic and/or gellatinolytic activity of MMPs. In a further embodiment, the tetracycline compound of the invention is administered to the surface of the skin (e.g., topically). In a further embodiment, the tetracycline compound of the invention used to treat a skin wound, and other such disorders as described in, for example, U.S. Pat. Nos. 5,827,840; 4,704,383; 4,935,412; 5,258,371; 5,308,8391 5,459,135; 5,532,227; and 6,015,804; each of which is incorporated herein by reference in its entirety.

In yet another embodiment, the tetracycline compound responsive state is an aortic or vascular aneurysm in vascular tissue of a subject (e.g., a subject having or at risk of having an aortic or vascular aneurysm, etc.). The tetracycline compound may by effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the tetracycline compounds of the invention are used to treat disorders described in U.S. Pat. Nos. 6,043,225 and 5,834,449, incorporated herein by reference in their entirety.

Bacterial infections may be caused by a wide variety of gram positive and gram negative bacteria. The compounds of the invention are useful as antibiotics against organisms which are resistant to other tetracycline compounds. The antibiotic activity of the tetracycline compounds of the invention may be determined using the method discussed in Example 2, or by using the in vitro standard broth dilution method described in Waitz, J. A., *National Commission for Clinical Laboratory Standards, Document M7-A2*, vol. 10, no. 8, pp. 13-20, $2^{nd}$ edition, Villanova, Pa. (1990).

The tetracycline compounds may also be used to treat infections traditionally treated with tetracycline compounds such as, for example, rickettsiae; a number of gram-positive and gram-negative bacteria; and the agents responsible for lymphogranuloma venereum, inclusion conjunctivitis, psittacosis. The tetracycline compounds may be used to treat infections of, e.g., *K. pneumoniae, Salmonella, E. hirae, A. baumanii, B. catarrhalis, H. influenzae, P. aeruginosa, E. faecium, E. coli, S. aureus* or *E. faecalis*. In one embodiment, the tetracycline compound is used to treat a bacterial infection that is resistant to other tetracycline antibiotic compounds. The tetracycline compound of the invention may be administered with a pharmaceutically acceptable carrier.

The language "effective amount" of the compound is that amount necessary or sufficient to treat or prevent a tetracycline compound responsive state. The effective amount can vary depending on such factors as the size and weight of the subject, the type of illness, or the particular tetracycline compound. For example, the choice of the tetracycline compound can affect what constitutes an "effective amount". One of ordinary skill in the art would be able to study the aforementioned factors and make the determination regarding the effective amount of the tetracycline compound without undue experimentation.

The invention also pertains to methods of treatment against microorganism infections and associated diseases. The methods include administration of an effective amount of one or more tetracycline compounds to a subject. The subject can be either a plant or, advantageously, an animal, e.g., a mammal, e.g., a human.

In the therapeutic methods of the invention, one or more tetracycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

The invention also pertains to pharmaceutical compositions comprising a therapeutically effective amount of a tetracycline compound (e.g., a 3, 10, and/or 12a substituted tetracycline compound) and, optionally, a pharmaceutically acceptable carrier.

The language "pharmaceutically acceptable carrier" includes substances capable of being coadministered with the tetracycline compound(s), and which allow both to perform their intended function, e.g., treat or prevent a tetracycline responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention that are basic in nature are capable of forming a wide variety of salts with various inorganic and organic acids. The acids that may be used to prepare pharmaceutically acceptable acid addition salts of the tetracycline compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a tetracycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other tetracycline compounds of the invention not specifically described in the foregoing experimental section can be accomplished using combinations of the reactions described above that will be apparent to those skilled in the art.

The preparation of other tetracycline compounds of the invention not specifically described in the foregoing experimental section can be accomplished using combinations of the reactions described above that will be apparent to those skilled in the art.

The tetracycline compounds of the invention that are acidic in nature are capable of forming a wide variety of base salts. The chemical bases that may be used as reagents to prepare pharmaceutically acceptable base salts of those tetracycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of tetracycline compounds of the invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, preferably under reduced pressure. Alternatively, a lower alkyl alcohol solution of the tetracycline compound of the invention may be mixed with an alkoxide of the desired metal and the solution subsequently evaporated to dryness.

The preparation of other tetracycline compounds of the invention not specifically described in the foregoing experimental section can be accomplished using combinations of the reactions described above that will be apparent to those skilled in the art.

The tetracycline compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a subject, e.g., a mammal. Preferred mammals include pets (e.g., cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating tetracycline responsive states can be used in the methods of the invention.

The tetracycline compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is derivatized with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule.

It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

Furthermore, the invention also pertains to the use of a tetracycline compound of formula I, for the preparation of a medicament. The medicament may include a pharmaceutically acceptable carrier and the tetracycline compound is an effective amount, e.g., an effective amount to treat a tetracycline responsive state.

EXEMPLIFICATION OF THE INVENTION

Compounds of the invention may be made as described below and/or by using literature techniques known to those of ordinary skill in the art.

Example 1

Synthesis of Compounds of the Invention

Synthesis of 3-Benzyloxysancycline

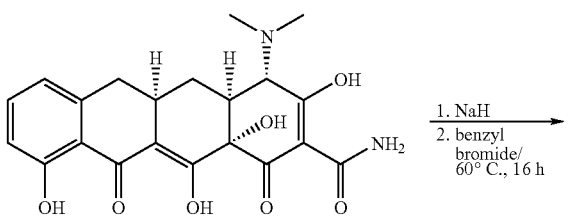

-continued

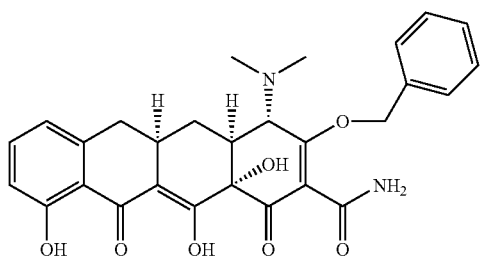

60% NaH in a mineral oil dispersion (100 mg, 2.5 mmol) was added in small portions to a stirred solution of sancycline (0.5 g, 1.20 mmol) in DMF (5 mL) at room temperature. The resulting suspension was stirred at room temperature for 5 minutes. Benzyl bromide (0.143 mL, 1.2 mmol) was added and heated at 60° C. for 16 hours. The reaction mixture was then cooled to room temperature and quenched with ether (100 mL). The ether was decanted and the remaining solid was dissolved in MeOH/water. The product was purified by preparative HPLC and converted to the HCl salt, yielding 3-benzyloxysancycline as a light yellow solid.

Synthesis of 3,10-Dibenzyloxysancycline

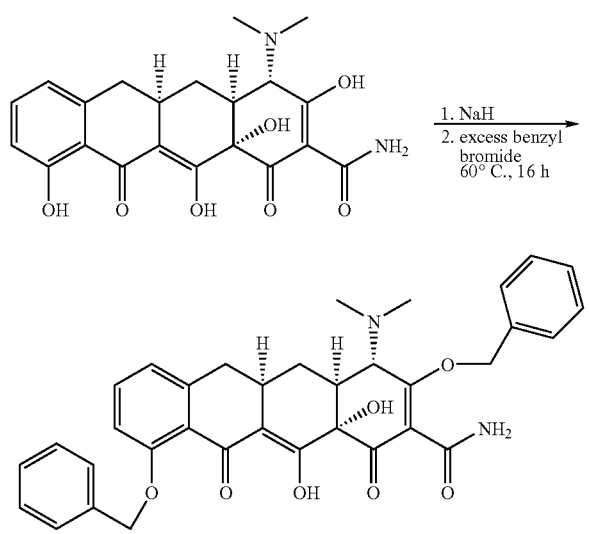

60% NaH in a mineral oil dispersion (192 mg, 4.8 mmol) was added in small portions to a stirred solution of sancycline (0.5 g, 1.20 mmol) in DMF (5 mL) at room temperature. The resulting suspension was stirred at room temperature for 5 minutes. Benzyl bromide (0.43 mL, 3.6 mmol) was added and the reaction mixture was heated at 60° C. for 1 hour. The reaction mixture was subsequently cooled to room temperature and quenched with ether (100 mL). The ether was the removed by decanting and the remaining solid was dissolved in MeOH/water. The product was purified by preparative HPLC and converted to the HCl salt to yield 3,10-dibenzyloxysancycline as a light yellow solid.

Synthesis of 10-propyloxysancycline

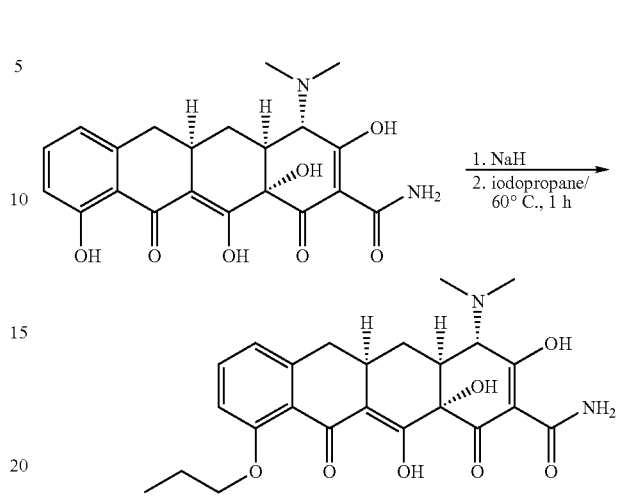

60% NaH in a mineral oil dispersion (192 mg, 4.8 mmol) was added in small portions to a stirred solution of sancycline (0.5 g, 1.20 mmol) in DMF (5 mL) at room temperature. The resulting suspension was stirred at room temperature for 5 minutes. Iodopropane (0.35 mL, 3.6 mmol) was added and heated at 60° C. for 1 hour. The reaction mixture was then cooled to room temperature and ether (100 mL) was added. The ether was decanted. The remaining solid was dissolved in MeOH/water and the product was purified by preparative HPLC and converted to the HCl salt to give 10-propyloxysancycline as a light yellow solid.

Synthesis of 10-Butyloxysancycline

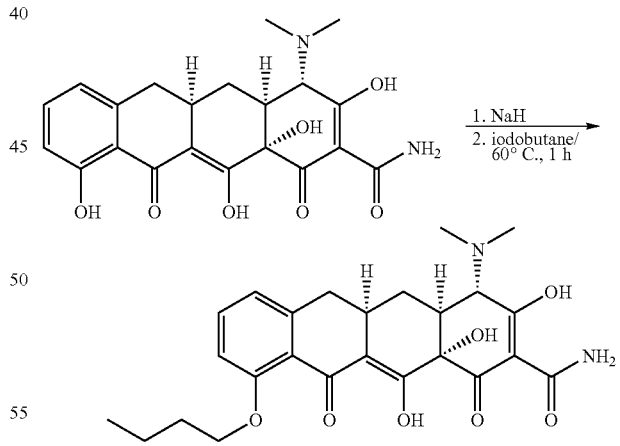

60% NaH in a mineral oil dispersion (192 mg, 4.8 mmol) was added in small portions to a stirred solution of sancycline (0.5 g, 1.20 mmol) in DMF (5 mL) at room temperature. The resulting suspension was stirred at room temperature for 5 minutes. Iodobutane (0.411 mL, 3.6 mmol) was added and heated at 60° C. for 1 hour. The reaction mixture was subsequently cooled to room temperature and quenched with ether (100 mL). The ether was then decanted and the remaining solid was dissolved in MeOH/water. The product was purified by preparative HPLC and converted to the HCl salt to give 10-butyloxysancycline as a light yellow solid.

Synthesis of 10-Butyloxyminocycline

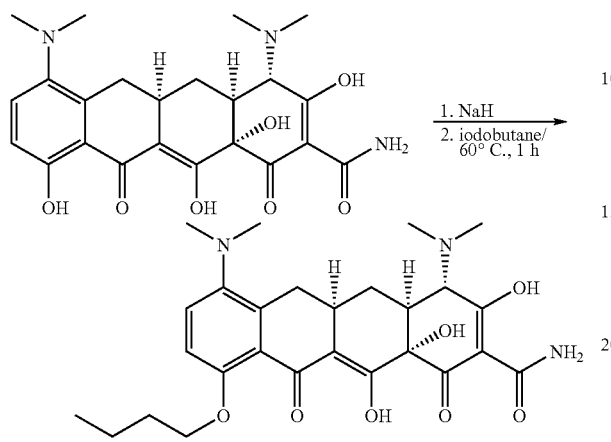

60% NaH in a mineral oil dispersion (152 mg, 3.8 mmol) was added in small portions to a stirred solution of minocycline HCl salt (0.5 g, 0.95 mmol) in DMF (5 mL) at room temperature. The resulting suspension was stirred at room temperature for 5 minutes. Iodobutane (0.325 mL, 2.85 mmol) was added and heated at 60° C. for 1 hour. The reaction mixture was cooled to room temperature and quenched with ether (100 mL). The ether was subsequently decanted and the remaining solid was dissolved in MeOH/water. The product was purified by preparative HPLC and converted to the HCl salt to give 10-butyloxyminocycline as an olive green solid.

Synthesis of 3,10-Dibenzyloxyminocycline

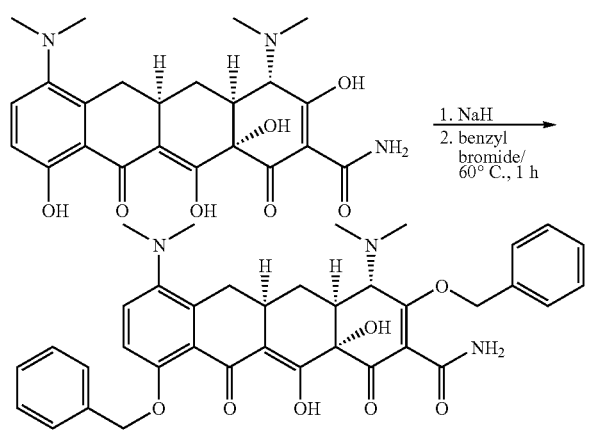

60% NaH in a mineral oil dispersion (152 mg, 3.8 mmol) was added in small portions to a stirred solution of minocycline HCl salt (0.5 g, 0.95 mmol) in DMF (5 mL) at room temperature. The resulting suspension was stirred at room temperature for 5 minutes. Benzyl bromide (0.34 mL, 2.84 mmol) was added and heated at 60° C. for 1 hour. The reaction mixture was then cooled to room temperature and quenched with ether (100 mL). The ether was then decanted and the remaining solid was dissolved in MeOH/water and the product was purified by preparative HPLC. The product was then converted to HCl salt to give 3,10-dibenzyloxyminocycline as an olive green solid.

Synthesis of Ethyl-3-(sancyclineoxy)acetate

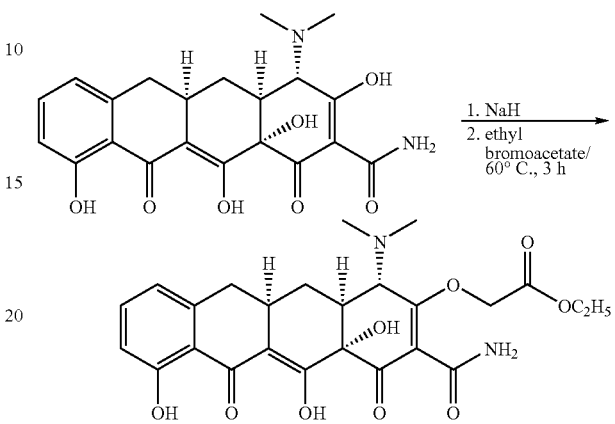

60% NaH in a mineral oil dispersion (192 mg, 4.8 mmol) was added in small portions to a stirred solution of sancycline (0.5 g, 1.2 mmol) in DMF (5 mL) at room temperature. The resulting suspension was stirred at room temperature for 5 minutes. Ethylbromo acetate (0.4 mL, 3.6 mmol) was added and the reaction mixture was heated at 60° C. for 1 hour. The reaction mixture was cooled to room temperature and quenched with ether (100 mL). The ether was decanted and the remaining solid was dissolved in MeOH/water. The product was purified by preparative HPLC and converted to the HCl salt to give ethyl-3-(sancyclineoxy)acetate as an olive green solid.

Synthesis of 7-Iodo-10-butyloxysancycline

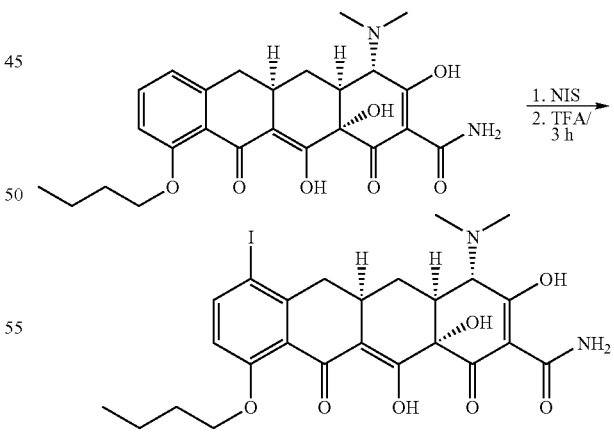

N-Iodosuccinimide (238 mg, 1.06 mmol) was added in two small portions to stirred solution of crude 10-butyloxysancycline (0.5 g) in trifluoroacetic acid (20 mL) at room temperature. The resulting dark brown solution was stirred at room temperature for 3 hours. The trifluoroacetic acid was evaporated under reduced pressure and the remaining gummy solid was dissolved in MeOH. The product was purified by preparative HPLC and converted to the HCl salt to give 7-iodo-10-butyloxysancycline as a light brown solid.

Synthesis of 10-Butyloxydoxycycline

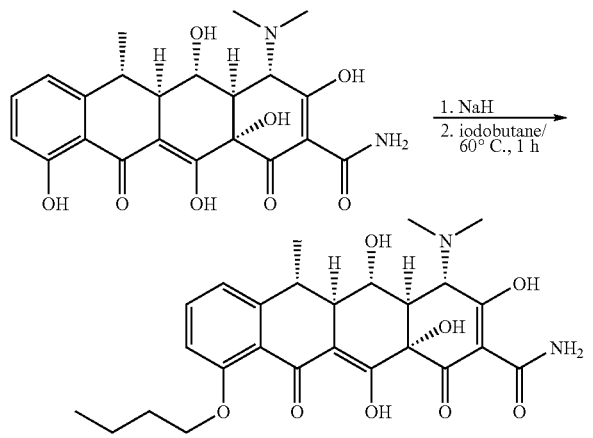

60% NaH in a mineral oil dispersion (173 mg, 4.3 mmol) was added in small portions to a stirred solution of doxycycline hydrate (0.5 g, 1.08 mmol) in DMF (5 mL) at room temperature. The resulting suspension was stirred at room temperature for 5 minutes. Iodobutane (0.37 mL, 3.24 mmol) was added and the reaction mixture was heated at 60° C. for 1 hour. The reaction mixture was then cooled to room temperature and quenched with ether (100 mL). The ether was decanted and the resulting gummy solid was dissolved in MeOH. The product was purified by preparative HPLC and converted to the HCl salt to give 10-butyloxydoxycycline as a light brown solid.

Synthesis of 3,10-Diallyloxysancycline

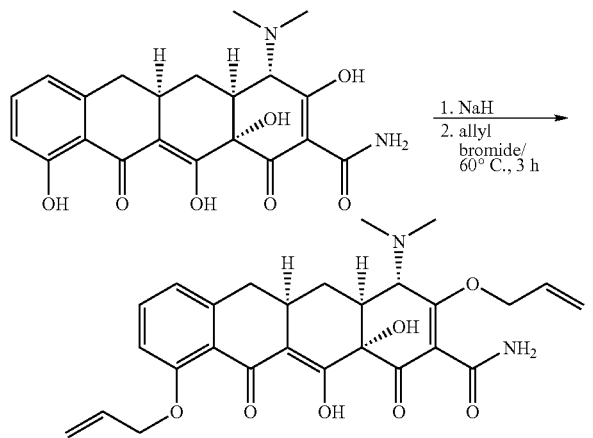

60% NaH in a mineral oil dispersion (192 mg, 4.8 mmol) was added in small portions to a stirred solution of sancycline (0.5 g, 1.2 mmol) in DMF (5 mL) at room temperature. The resulting suspension was stirred at room temperature for 5 minutes. Allyl bromide (0.311 mL, 3.6 mmol) was added and heated at 60° C. for 1 hour. The reaction mixture was cooled to room temperature and quenched with ether (100 mL). The ether was decanted and the remaining gummy solid was dissolved in MeOH. The product was purified by preparative HPLC and converted to the HCl salt to give 3,10-diallyloxysancycline as a pale brown solid.

Synthesis of 3-Benzyloxy-7-iodosancycline

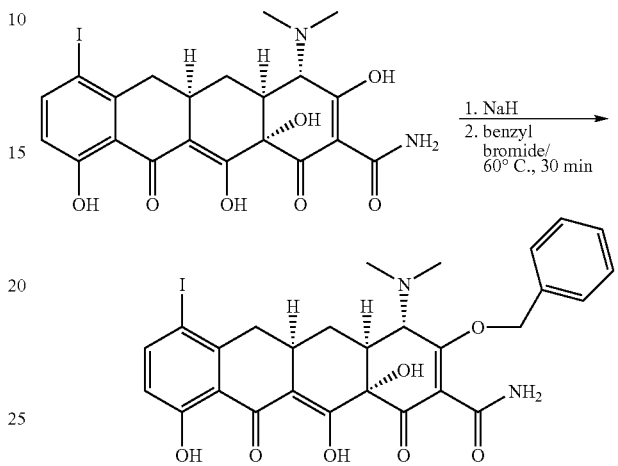

60% NaH (121 mg, 3.04 mmol) was added in small portions to a stirred solution of 7-iodosancycline TFA salt (0.5 g, 0.76 mmol) in DMF (10 mL) at room temperature. The resulting suspension was stirred at room temperature for 5 minutes. Benzyl bromide (0.277 mL, 2.28 mmol) was added and heated at 60° C. for 30 minutes. The reaction mixture was then cooled to room temperature and quenched with ether (100 mL). The ether was decanted and the remaining solid was dissolved in MeOH. The product was purified by preparative HPLC and converted to the HCl salt to give 3-benzyloxy-7-iodosancycline as a yellow solid.

Synthesis of 3-Benzyloxy-7-(3'-trifluoromethylphenyl)sancycline

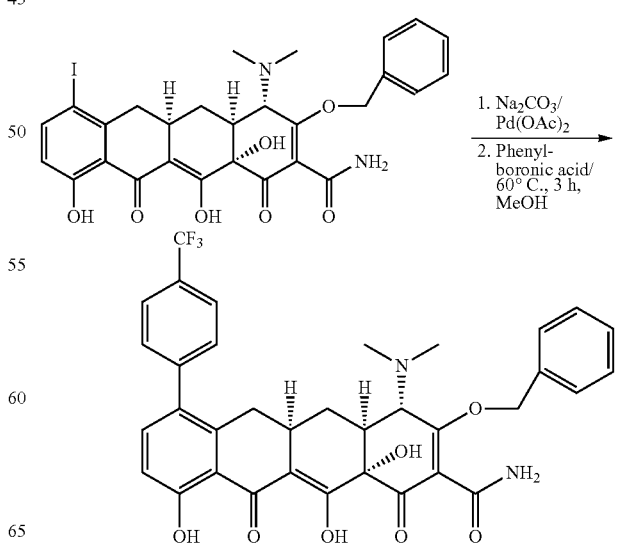

A solution of sodium carbonate (670 mg, 6.32 mmol) in water (5 mL) was added to a stirred suspension of 7-iodo-3-benzyloxysancycline (1.00 g, 1.58 mmol) and Pd(OAc)$_2$ (100 mg, 0.44 mmol) in methanol (10 mL) at 60° C. under nitrogen. The resulting suspension was stirred at 60° C. for 10 min. 4-Trifluoromethylphenyl boronic acid (0.6 g, 3.16 mmol) in methanol (10 mL) was then added and the reaction mixture was heated at 60° C. for 3 hours under nitrogen. The warm reaction mixture was filtered and concentrated. The crude product was purified by preparative HPLC and converted to the HCl salt to give 3-benzyloxy-7-(3'-trifluoromethylphenyl)sancycline as a pale brown solid.

Synthesis of Ethyl (7-iodo 3-sancyclineoxy)acetate

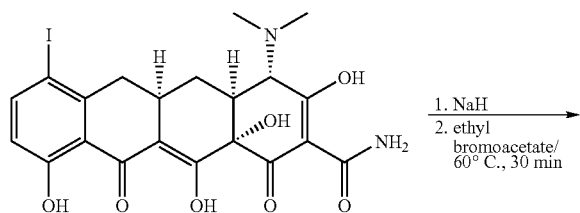

60% NaH (121 mg, 3.04 mmol) was added in small portions to a stirred solution of 7-iodosancycline TFA salt (0.5 g, 0.76 mmol) in DMF (10 mL) at room temperature. The resulting suspension was stirred at room temperature for 5 minutes. Ethyl bromoacetate (0.252 mL, 2.28 mmol) was added and heated at 60° C. for 2 hours. The reaction mixture was then cooled to room temperature and quenched with ether (100 mL). The ether was then decanted and the solid was dissolved in MeOH. The product was purified by preparative HPLC and the resulting solid was converted to HCl salt to give ethyl (7-iodo 3-sancyclineoxy)acetate as a yellow solid.

Synthesis of 12a-methylamino Doxycycline

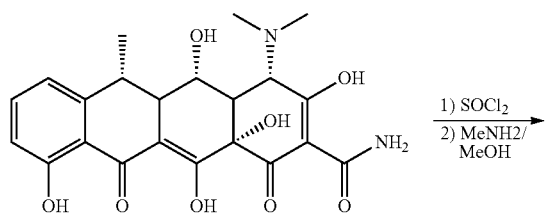

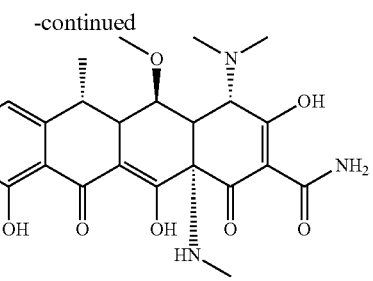

2 g of Doxycycline was dissolved in 10 ml of thionyl chloride. The reaction mixture was heated at 55 C for ~2 hrs. The solution was cooled in an ice-bath and then added slowly to ice-cold ether. Brownish solid precipitated out which was filtered and dried.

300 mg of SOCl$_2$-doxycycline complex was dissolved in 3 ml of 2M solution of methylamine in methanol. The starting material disappeared rapidly and a new peak appeared with an M+H of 427. As the reaction proceeded, this material converted to a new peak with lower retention time and the mass showed 440. This product was isolated by preparative HPLC and identified by 2D NMR to be the product, exhibiting characteristic NMR peaks and NOE interactions.

Example 2

In Vitro Minimum Inhibitory Concentration (MIC) Assay

The following assay is used to determine the efficacy of tetracycline compounds against common bacteria. 2 mg of each compound is dissolved in 100 µl of DMSO. The solution is then added to cation-adjusted Mueller Hinton broth (CAMHB), which results in a final compound concentration of 200 µg per ml. The tetracycline compound solutions are diluted to 50 µL volumes, with a test compound concentration of 0.098 µg/ml. Optical density (OD) determinations are made from fresh log-phase broth cultures of the test strains. Dilutions are made to achieve a final cell density of $1 \times 10^6$ CFU/ml. At OD=1, cell densities for different genera should be approximately:

| | |
|---|---|
| *E. coli* | $1 \times 10^9$ CFU/ml |
| *S. aureus* | $5 \times 10^8$ CFU/ml |
| *Enterococcus* sp. | $2.5 \times 10^9$ CFU/ml |

50 µl of the cell suspensions are added to each well of microtiter plates. The final cell density should be approximately $5 \times 10^5$ CFU/ml. These plates are incubated at 35° C. in an ambient air incubator for approximately 18 hr. The plates are read with a microplate reader and are visually inspected when necessary. The MIC is defined as the lowest concentration of the tetracycline compound that inhibits growth.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The invention claimed is:
1. A compound of Formula I:

$$\text{(I)}$$

wherein:
X is CHC($R^{13}$Y'Y) or C$R^6$'$R^6$;
$R^{2''}$ is —C(=O)N$R^2$$R^{2'}$ or —CN;
$R^2$, $R^{2'}$, $R^{4a}$ and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic or heteroaromatic;
$R^3$, $R^{11}$ and $R^{12''}$ are each independently hydrogen, alkyl, alkenyl, aryl, alkynyl, arylalkyl, acetyl, alkylcarbonyl, alkenylcarbonyl, arylcarbonyl, alkynylcarbonyl, alkyloxycarbonyl, alkenyloxycarbonyl, alkynyloxycarbonyl, aryloxycarbonyl, alkylaminocarbonyl, alkenylaminocarbonyl, alkynylaminocarbonyl, arylaminocarbonyl, alkylthiocarbonyl, alkenylthiocarbonyl, alkynylthiocarbonyl, arylthiocarbonyl, alkyloxythiocarbonyl, alkenyloxythiocarbonyl, alkynyloxythiocarbonyl, aryloxythiocarbonyl, alkylaminothiocarbonyl, alkenylaminothiocarbonyl, alkynylaminothiocarbonyl, arylaminothiocarbonyl, alkylthiothiocarbonyl, alkenylthiothiocarbonyl, alkynylthiothiocarbonyl or arylthiothiocarbonyl;
$R^{10}$ is hydrogen, alkenyl, aryl, alkynyl, arylalkyl, alkenylcarbonyl, arylcarbonyl, alkynylcarbonyl, alkyloxycarbonyl, alkenyloxycarbonyl, alkynyloxycarbonyl, aryloxycarbonyl, alkylaminocarbonyl, alkenylaminocarbonyl, alkynylaminocarbonyl, arylaminocarbonyl, alkylthiocarbonyl, alkenylthiocarbonyl, alkynylthiocarbonyl, arylthiocarbonyl, alkyloxythiocarbonyl, alkenyloxythiocarbonyl, alkynyloxythiocarbonyl, aryloxythiocarbonyl, alkylaminothiocarbonyl, alkenylaminothiocarbonyl, alkynylaminothiocarbonyl, arylaminothiocarbonyl, alkylthiothiocarbonyl, alkenylthiothiocarbonyl, alkynylthiothiocarbonyl or arylthiothiocarbonyl;
$R^{12}$ is hydrogen, alkyl, alkenyl, aryl, alkynyl, arylalkyl, alkenylcarbonyl, alkynylcarbonyl, alkyloxycarbonyl, alkenyloxycarbonyl, alkynyloxycarbonyl, aryloxycarbonyl, alkenylaminocarbonyl, alkynylaminocarbonyl, alkylthiocarbonyl, alkenylthiocarbonyl, alkynylthiocarbonyl, arylthiocarbonyl, alkyloxythiocarbonyl, alkenyloxythiocarbonyl, alkynyloxythiocarbonyl, aryloxythiocarbonyl, alkylaminothiocarbonyl, alkenylaminothiocarbonyl, alkynylaminothiocarbonyl, arylaminothiocarbonyl, alkylthiocarbonyl, alkenylthiothiocarbonyl, alkynylthiothiocarbonyl or arylthiothiocarbonyl, provided that at least one of $R^3$, $R^{10}$, $R^{11}$ or $R^{12}$ is not hydrogen when $R^{12'}$ is O$R^{12}$;
$R^4$ and $R^{4'}$ are each independently N$R^{4a}$$R^{4b}$, alkyl, alkenyl, alkynyl, hydroxyl, halogen or hydrogen;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy or aryl carbonyloxy;
$R^6$ and $R^{6'}$ are each independently hydrogen, hydroxyl, halogen, thiol, alkyl, alkenyl, alkynyl, aryl, alkoxy, alkylthio, alkylsulfinyl, alkylsulfonyl, alkylamino or arylalkyl;
$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, arylalkenyl, arylalkynyl, acyl, aminoalkyl, heterocyclic, thionitroso or —(CH$_2$)$_{1-3}$NR$^{7c}$C(=W')WR$^{7a}$;
$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso or —(CH$_2$)$_{0-3}$NR$^{8c}$C(=E')ER$^{8a}$;
$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso or —(CH$_2$)$_{0-3}$NR$^{9c}$C(=Z')ZR$^{9a}$;
$R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$ and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic or heteroaromatic;
$R^{12'}$ is O$R^{12}$ or N$R^{12}$$R^{12''}$;
$R^{13}$ is hydrogen, hydroxyl, alkyl, alkenyl, alkynyl, alkoxy, alkylthio, aryl, alkylsulfinyl, alkylsulfonyl, alkylamino or arylalkyl;
E is CR$^{8d}$R$^{8e}$; S, NR$^{8b}$ or O;
E' is O, NR$^{8f}$ or S;
W is CR$^{7d}$R$^{7e}$, S, NR$^{7b}$ or O;
W' is O, NR$^{7f}$ or S;
Z is CR$^{9d}$R$^{9e}$, S, NR$^{9b}$ or O;
Z' is O, S or NR$^{9f}$; and
Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino or arylalkyl, or pharmaceutically acceptable salts, esters or enantiomers thereof.

2. The compound of claim 1, wherein X is CR$^6$R$^{6'}$; R$^2$, R$^{2'}$, R$^6$, R$^{6'}$, R$^8$ and R$^{11}$ are each hydrogen; and R$^5$ is hydroxyl or hydrogen.

3. The compound of claim 2, wherein R$^4$ is dialkylamino; and R$^{4'}$ and R$^5$ are each hydrogen.

4. The compound of claim 1, wherein R$^3$ is hydrogen, alkyl, alkenyl, aryl, acetyl, arylalkyl, alkynyl, alkylcarbonyl, alkenylcarbonyl, arylcarbonyl, alkynylcarbonyl, alkyloxycarbonyl, alkenyloxycarbonyl, alkynyloxycarbonyl, aryloxycarbonyl, alkylaminocarbonyl, alkenylaminocarbonyl, alkynylaminocarbonyl, arylaminocarbonyl, alkylthiocarbonyl, alkenylthiocarbonyl, alkynylthiocarbonyl, arylthiocarbonyl, alkyloxythiocarbonyl, alkenyloxythiocarbonyl, alkynyloxythiocarbonyl, aryloxythiocarbonyl, alkylaminothiocarbonyl, alkenylaminothiocarbonyl, alkynylaminothiocarbonyl, arylaminothiocarbonyl, alkylthiothiocarbonyl, alkenylthiothiocarbonyl, alkynylthiothiocarbonyl or aryithiothiocarbonyl.

5. The compound of claim 4, wherein R$^3$ is benzyl.
6. The compound of claim 4, wherein R$^3$ is alkyl.
7. The compound of claim 4, wherein R$^3$ is acetyl.
8. The compound of claim 4, wherein R$^3$ is alkenyl.
9. The compound of claim 4, wherein R$^3$ is hydrogen.

10. The compound of claim 1, wherein $R^{10}$ is hydrogen, alkenyl, aryl, arylalkyl, alkynyl, alkenylcarbonyl, arylcarbonyl, alkynylcarbonyl, alkyloxycarbonyl, alkenyloxycarbonyl, alkynyloxycarbonyl, aryloxycarbonyl, alkylaminocarbonyl, alkenylaminocarbonyl, alkynylaminocarbonyl, arylaminocarbonyl, alkylthiocarbonyl, alkenylthiocarbonyl, alkynylthiocarbonyl, arylthiocarbonyl, alkyloxythiocarbonyl, alkenyloxythiocarbonyl, alkynyloxythiocarbonyl, aryloxythiocarbonyl, alkylaminothiocarbonyl, alkenylaminothiocarbonyl, alkynylaminothiocarbonyl, arylaminothiocarbonyl, alkylthiothiocarbonyl, alkenylthiothiocarbonyl, alkynylthiothiocarbonyl or arylthiothiocarbonyl.

11. The compound of claim 10, wherein $R^{10}$ is benzyl.

12. The compound of claim 10, wherein $R^{10}$ is alkenyl.

13. The compound of claim 10, wherein $R^{10}$ is hydrogen.

14. The compound of claim 1, wherein $R^{12}$ is hydrogen, alkyl, alkenyl, aryl, arylalkyl, alkynyl, alkenylcarbonyl, alkynylcarbonyl, alkyloxycarbonyl, alkenyloxycarbonyl, alkynyloxycarbonyl, aryloxycarbonyl, alkenylaminocarbonyl, alkynylaminocarbonyl, alkylthiocarbonyl, alkenylthiocarbonyl, alkynylthiocarbonyl, arylthiocarbonyl, alkyloxythiocarbonyl, alkenyloxythiocarbonyl, alkynyloxythiocarbonyl, aryloxythiocarbonyl, alkylaminothiocarbonyl, alkenylaminothiocarbonyl, alkynylaminothiocarbonyl, arylaminothiocarbonyl, alkylthiothiocarbonyl, alkenylthiothiocarbonyl, alkynylthiothiocarbonyl or arylthiothiocarbonyl.

15. The compound of claim 14, wherein $R^{12}$ is benzyl.

16. The compound of claim 14, wherein $R^{12}$ is hydrogen.

17. A compound selected from the group consisting of:

-continued

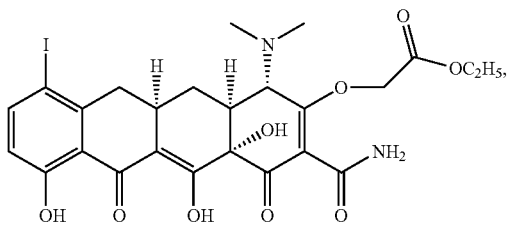

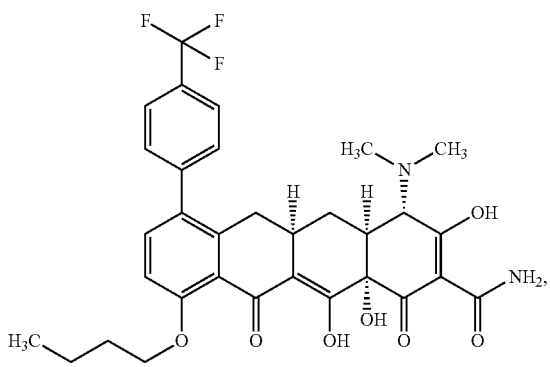

-continued

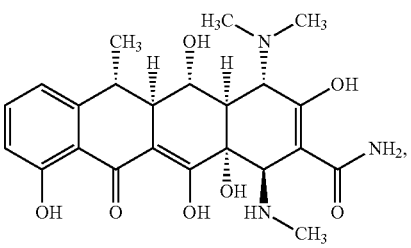

or pharmaceutically acceptable salts, esters or enantiomers thereof.

18. A method for treating a tetracycline responsive state in a subject, comprising administering to said subject a compound of claim 1 or 17, such that said tetracycline responsive state is treated.

19. The method of claim 18, wherein said compound is non-antibacterial.

20. The method of claim 18 wherein said tetracycline responsive state is an inflammatory process associated state, a cancer, a lung injury, an eye disorder, a stroke or a neurological disorder.

21. The method of claim 20, wherein said neurological disorder is Alzheimer's disease, Huntington's disease, Parkinson's disease, amylotropic lateral sclerosis or multiple sclerosis.

22. A pharmaceutical composition comprising a therapeutically effective amount of a compound of claim 1 or 17, and a pharmaceutically acceptable carrier.

23. A compound selected from the group consisting of:

-continued
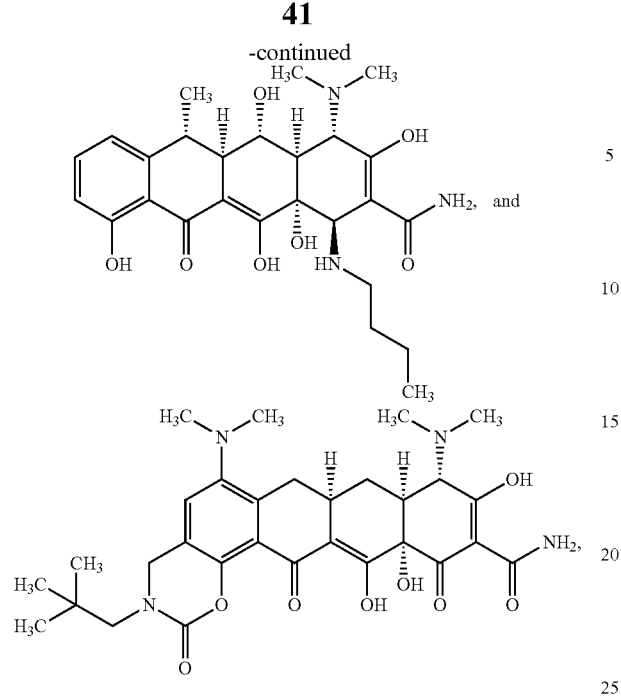
or pharmaceutically acceptable salts, esters or enantiomers thereof.
24. A pharmaceutical composition comprising a therapeutically effective amount of a compound of claim 23, and a pharmaceutically acceptable carrier.
* * * * *